(12) United States Patent
Hoch et al.

(10) Patent No.: US 9,863,949 B2
(45) Date of Patent: Jan. 9, 2018

(54) METHOD FOR PREDICTING AND EVALUATING RESPONSIVENESS TO CANCER TREATMENT WITH DNA-DAMAGING CHEMOTHERAPEUTIC AGENTS

(71) Applicant: NEKTAR THERAPEUTICS, San Francisco, CA (US)

(72) Inventors: Ute Hoch, San Francisco, CA (US); Christine Taylor Brew, Pacifica, CA (US); Stephen David Harrison, Albany, CA (US); Dennis G. Fry, Pacifica, CA (US); Darren W. Davis, Houston, TX (US)

( * ) Notice: Subject to any disclaimer, the term of this patent is extended or adjusted under 35 U.S.C. 154(b) by 0 days.

(21) Appl. No.: 14/292,613

(22) Filed: May 30, 2014

(65) Prior Publication Data

US 2014/0357659 A1 Dec. 4, 2014

Related U.S. Application Data

(60) Provisional application No. 61/829,948, filed on May 31, 2013.

(51) Int. Cl.
| | | |
|---|---|---|
| G01N 33/573 | (2006.01) | |
| G01N 33/574 | (2006.01) | |
| G01N 33/68 | (2006.01) | |
| A61K 47/48 | (2006.01) | |

(52) U.S. Cl.
CPC ..... *G01N 33/573* (2013.01); *A61K 47/48215* (2013.01); *G01N 33/574* (2013.01); *G01N 33/68* (2013.01); *G01N 2333/99* (2013.01); *G01N 2500/10* (2013.01); *G01N 2800/52* (2013.01)

(58) Field of Classification Search
None
See application file for complete search history.

(56) References Cited

U.S. PATENT DOCUMENTS

| | | | |
|---|---|---|---|
| 6,258,540 B1 * | 7/2001 | Lo | C12Q 1/6879 435/440 |
| 6,355,623 B2 * | 3/2002 | Seidman | A61K 31/52 514/263.4 |
| 7,744,861 B2 | 6/2010 | Zhao et al. | |
| 8,263,062 B2 | 9/2012 | Zhao et al. | |
| 2007/0071762 A1 * | 3/2007 | Ts'o | G01N 33/57484 424/155.1 |

FOREIGN PATENT DOCUMENTS

| | | |
|---|---|---|
| WO | WO 2007/035842 A2 | 3/2007 |
| WO | WO 2007/092646 A2 | 8/2007 |
| WO | WO 2011/063156 A2 | 5/2011 |

OTHER PUBLICATIONS

Hoch et al. (J. Clin. Oncology May 20, 2013 31(15, Suppl. 1): Abs. No. 1087).*
Adlard et al. (The Lancet Oncology Feb. 2002 3: 75-81).*
PCT International Search Report corresponding to PCT Application No. PCT/US2014/040382 date of mailing Nov. 14, 2014.
Ataka et al., "Topoisomerase I Protein Expression and Prognosis of Patients with Colorectal Cancer", Yonago Acta medica, vol. 50, pp. 81-87, (2007).
Avril et al., "Response to Therapy in Breast Cancer", J. Nucl. Med., vol. 50, pp. 55S-63S, (2009).
Burgess et al., "Topoisomerase levels determine chemotherapy response in vitro and in vivo", PNAS, vol. 105, No. 26, pp. 9053-9058, (Jul. 1, 2008).
Cen et al., "Circulating tumor cells in the diagnosis and management of pancreatic cancer", Biochimica et Biophysica Acta 1826, pp. 350-356, (2012).
Cho, "Contribution of oncoproteomics to cancer biomarker discovery", Molecular Cancer, vol. 6, No. 25, pp. 1-13, (2007).
Cohen et al., "Relationship of Circulating Tumor Cells to Tumor Response, Progression-Free Survival, and Overall Survival in Patients With Metastatic Colorectal Cancer", J. Clin. Oncol. vol. 26, No. 19, pp. 3213-3221, (Jul. 1, 2008).
De Bono et al., "Potential Applications for Circulating Tumor Cells Expressing the Insulin-Like Growth Factor-I Receptor", Clin. Cancer Res., vol. 13, No. 12, pp. 3611-3616, (Jun. 15, 2007).
Desitter et al., "A New Device for Rapid Isolation by Size and Characterization of Rare Circulating Tumor Cells", Anticancer Research, vol. 31, pp. 427-441, (2011).
Froelich-Ammon et al., "Topoisomerase Poisons: Harnessing the Dark side of Enzyme Mechanism", The Journal of Biological Chemistry, vol. 270, No. 37, Issue of Sep. 15, pp. 21429-21432, (1995).
Gazzaniga et al., "Chemosensitivity profile assay of circulating cancer cells: prognostic and predictive value in epithelial tumors", Int. J. Cancer, vol. 126, pp. 2437-2447, (2010).
Gradilone et al., "Circulating tumor cells (CTCs) in metastatic breast cancer (MBC): prognosis, drug resistance and phenotypic characterization", vol. 22, pp. 86-92, (2011).
Gupta et al., "ApoStream™, a new dielectrophoretic device for antibody independent isolation and recovery of viable cancer cells from blood", Biomicrofluidics, vol. 6, pp. 024133-1-024133-14, (2012).
Horisberger et al., "Topoisomerase I expression correlates to response to neoadjuvant irinotecan-based chemoradiation in rectal cancer", Anti-Cancer Drugs, vol. 20, pp. 519-524, (2009).
Maheswaran et al., "Detection of Mutation in EGFR in Circulating Lung-Cancer Cells", N. Engl. J. Med., vol. 359, pp. 366-377, (2008).

(Continued)

*Primary Examiner* — Peter J Reddig
(74) *Attorney, Agent, or Firm* — Susan T. Evans; Mark A. Wilson

(57) ABSTRACT

Provided herein are methods directed to the prediction and early assessment of the efficacy of cancer treatment regimens, in particular in patients undergoing therapy with a DNA-damaging chemotherapeutic agent, by determining expression levels of certain proteins found to be useful as biomarkers in circulating tumor cells obtained from the patient both prior to and post-treatment.

4 Claims, 1 Drawing Sheet

(56) References Cited

OTHER PUBLICATIONS

Nagrath et al., "Isolation of rare circulating tumour cells in cancer patients by microchip technology", Nature, vol. 450, No. 20, pp. 1235-1239, (Dec. 27, 2007).
Ozkumur et al., "Inertial Focusing for Tumor Antigen-Dependent and -Independent Sorting of Rare Circulating Tumor Cells", Science Translational Medicine, vol. 5, Issue 179, pp. 1-11, (Apr. 3, 2013).
Pantel et al., "The clinical significance of circulating tumor cells", Nature Clinical Practice Oncology, vol. 4, No. 2, pp. 62-63, (Feb. 2007).
Patnaik, et al., "EZN-2208, a novel anticancer agent, in patients with advanced malignancies: a Phase 1 dose-escalation study", Poster C221, Presented at AACR-NCI-EORTC, 2 pages, (Nov. 2009).
Pfister et al., "Topoisomerase I levels in the NCI-60 cancer cell line panel determined by validated ELISA and microarray analysis and correlation with indenoisoquinoline sensitivity", Mol. Cancer Ther., vol. 8, No. 7, pp. 1878-1884, (Jul. 2009).
Sapra, et al., "Marked therapeutic efficacy of a novel poly(ethylene-glycol) conjugated SN38 conjugate in xenograft models of breast and colorectal cancers", Abstract# 145, 1 page. (No date).
Therasse et al., "New Guidelines to Evaluate the Response to Treatment in Solid Tumors", Journal of the National Cancer Institute, vol. 92, No. 3, pp. 205-216, (Feb. 2, 2000).
Wang et al., "Monitoring Drug-Induced γH2AX as a Pharmacodynamic Biomarker in Individual Circulating Tumor Cells", Clin. Cancer Res., vol. 16, pp. 1073-1084, (2010).
Enzon Pharmaceuticals, Macromolecular Engineering Technologies, 16 pages, (2004).
Nektar™—Transforming Therapeutics, Nektar Molecule Engineering: Polyethylene Glycol and Derivatives for Advanced PEGylation, 24 pages, Catalog—2003, (Jul. 2003).
Nektar™—Transforming Therapeutics, Nektar Advanced PEGylation: Polyethylene Glycol and Derivatives for Advanced PEGylation, 27 pages, Catalog—2004, (Jul. 2004).
Nektar™—Transforming Therapeutics, Nektar Advanced PEGylation: Polyethylene Glycol and Derivatives for Advanced PEGylation, 33 pages, (Catalog 2005-2006).
NOF Corporation, PEG Derivatives, Phospholipid and Drug Delivery Materials for Pharmaceuticals, 46 pages, Catalogue 2003-1$^{st}$, (Jan. 2003).
NOF Corporation, PEG Derivatives, Phospholipid and Drug Delivery Materials for Pharmaceuticals, 27 pages, Catalogue 2003-2$^{nd}$, (Mar. 2004).
NOF Corporation, PEG Derivatives, Phospholipids and Drug Delivery Materials for Pharmaceutical Products and Formulations, 60 pages, Catalogue Ver. 8, (Apr. 2006).
Polypure Products, PEG amines; PEG acids and amino acids; PEG thiols and disulfides; BIOTINS, 5 pages, (Apr. 2004).
Polypure Products, PEG amines; PEG acids and amino acids; PEG thiols and disulfides; BIOTINS, 5 pages, (Apr. 2005).
Quanta Biodesign, Labeling, Derivatization and Crosslinking Reagents for Biological and Related Materials with dPEG™, 38 pages, (Mar. 12, 2004).
Quanta Biodesign, Labeling, Modification and Crosslinking Reagents incorporating our unique monodispersed dPEG™ Technology, 31 pages, (Nov. 5, 2004).
Quanta Biodesign, Ltd., Leading innovator, producer and provider of monodisperse discrete PEG™ (dPEG™) derivatives, (Product Catalog), 26 pages, (Updated: Jul. 18, 2005).
Quanta Biodesign, Ltd., Leading innovator, producer and provider of monodisperse discrete Peg™ (dPEG™) derivatives, (Product Catalog), 26 pages, (Updated: Nov. 17, 2005).
Shearwater Polymers, Inc., Polyethylene Glycol Derivatives, 50 pages, Catalog—(Mar. 1995).
Shearwater Polymers, Inc., Polyethylene Glycol Derivatives, 55 pages, Catalog 1997-1998, (Jul. 1997).
Shearwater Polymers, Inc., Polyethylene Glycol and Derivatives: Functionalized Biocompatible Polymers for Research and Pharmaceuticals, 50 pages, Catalog—(Jan. 2000).
Shearwater Corporation, Polyethylene Glycol and Derivatives for Biomedical Applications, 20 pages, Catalog—(Jul. 2001).
PCT International Preliminary Report on Patentability corresponding to PCT Application No. PCT/US2014/040382 dated Dec. 10, 2015.
European Communication corresponding to European Patent Application No. 14 733 908.9 dated Mar. 9, 2017.

* cited by examiner

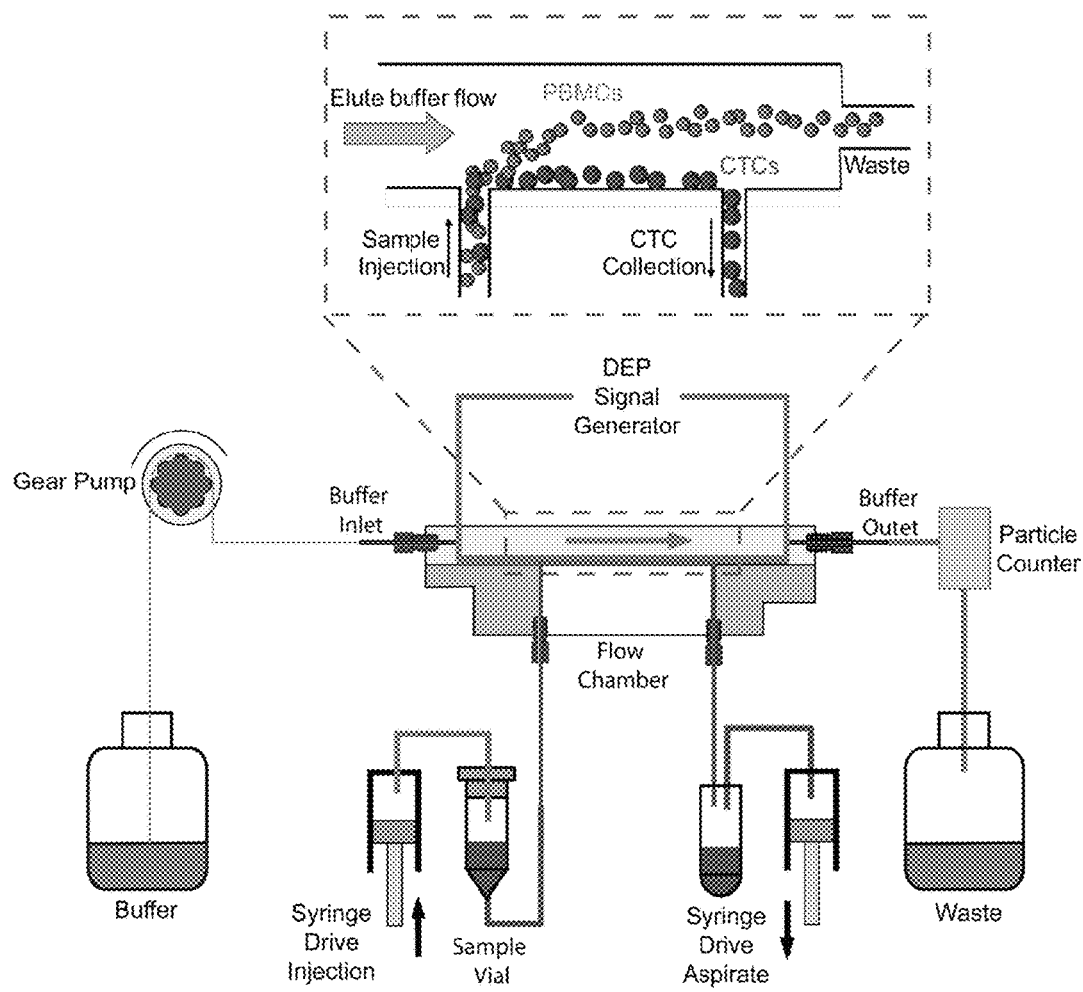
(prior art)

METHOD FOR PREDICTING AND EVALUATING RESPONSIVENESS TO CANCER TREATMENT WITH DNA-DAMAGING CHEMOTHERAPEUTIC AGENTS

CROSS REFERENCE TO RELATED APPLICATIONS

This application claims the benefit of priority under 35 U.S.C. §119(e) to U.S. Provisional Patent Application No. 61/829,948, filed May 31, 2013, the disclosure of which is incorporated herein by reference in its entirety.

FIELD

This invention relates to (among other things) the field of cancer chemotherapy. More specifically, the methods provided herein relate to cancer treatment and prognosis, and even more particularly, to methods for (i) predicting the responsiveness of a patient to treatment with a chemotherapeutic agent prior to, and over the course of treatment, along with post-treatment monitoring, and (ii) assessing the efficacy and overall response of a patient to therapy with one or more particular chemotherapeutic agents, preferably at an early stage of treatment.

BACKGROUND

More than 11 million people are diagnosed with cancer each year; it is estimated that there will be 16 million new cases every year by 2020 (Cho, WSC., *Mol Cancer* 2007; 6:25). Traditionally, pathologists have played a major role in the initial diagnosis of cancer, and in the morphologic classification and evaluation of the responsiveness of the patient to therapy, based upon analysis of tissue samples (i.e., serial biopsies).

More recently, there has been a significant advancement of our understanding of the molecular origins of different types of cancer and characteristics of tumor aggressiveness, based upon a major expansion of genomic and proteomic data. Cancer cells display a broad spectrum of genetic alterations that include gene rearrangements, point mutations and gene amplifications, which lead to disturbances in molecular pathways regulating cell growth, survival and metastasis. When such changes manifest themselves in patients (from a small percentage to a majority of patients) having a cancerous tumor, or receiving treatment with a chemotherapeutic agent having a particular mechanism of action, discovery and quantification of these changes can be used to identify biomarkers for detecting and developing targeted therapies, and for predicting the clinical response to chemotherapeutic drugs used to treat the disease. The identification of new predictive biomarkers can provide invaluable assistance to clinicians in minimally-invasively and rapidly predicting a patient's response to therapy, selecting the best treatment modality, monitoring response to treatment over the course of therapy, as well as post-therapy, to thereby improve the likelihood of overall and recurrence-free survival. The advantages of the above cannot be understated.

Recent technologies have allowed the detection and isolation of circulating tumor cells (CTCs). CTCs are rare cells present in the blood in numbers as low as one CTC per $10^6$-$10^7$ leucocytes. Historically, the detection and capture of such cells has been challenging (Gupta, et al., *Biomicrofluidics* 6, 024133 (2012)). Techniques currently used for CTC capture include immunomagnetic separation (Cohen, S. J., et al., *J. Clin. Oncol.* 26, 3213 (2008); Maheswaran, S., et al., *N. Engl. J. Med.* 359, 366 (2008), membrane filters (Desitter, I., et al., *Anticancer Res.* 31, 427 (2011), micro-electro-mechanical system chips (Nagrath, S., et al., *Nature* 450, 1235 (2007)), and dielectrophoretic field-flow fractionation (DEP-FFF) technology (Gupta, V., et al, ibid.).

Generally, CTC detection methods are composed of the following two steps: an enrichment (isolation) process and detection (identification) process (cytometric and nucleic acid techniques), which may or may not be separate from enrichment. Genetic and molecular characterization of CTCs is typically conducted by fluorescent in situ hybridization (FISH), comparative genomic hybridization (CGH), PCR-based techniques, and biomarker immunofluorescent staining. Normally absent from the peripheral blood of a healthy donor, CTC counts have been described to correlate negatively with progression-free survival and overall survival in patients with metastatic, colorectal, breast, and prostate cancer (Gupta, V., et al., ibid.).

Although numbers of CTCs have previously been correlated with patient survival, CTC isolation from a patient blood sample and subsequent molecular analysis of such cells has not been previously reported for the prediction of responsiveness of a patient to treatment with a particular type of chemotherapeutic agent as provided herein, nor have such analyses been widely used to provide a minimally invasive method to predict, guide and monitor the results of cancer therapy.

In certain cancers such as breast cancer, monitoring a patient's response to treatment is an essential component of therapy, since the degree of response can provide important prognostic information related to disease-free and overall survival. Histopathology provides an accurate assessment of treatment efficacy on the basis of the extent of residual tumor and regressive changes within the tumor tissue. However, only 20% of breast cancer patients achieve a pathologic complete response, a fact that necessitates methods for monitoring therapeutic effectiveness early during therapy (Avril, N. et al., *The Journal of Nuclear Medicine,* 50 (5) Suppl., May 2009, 55S-63S). Early identification of ineffective therapy may also be useful in patients with metastatic breast and other types of cancer due to the number of palliative treatment options. New methods for predicting therapeutic effectiveness prior to and over the course of therapeutic treatment of various cancers, especially methods that are rapid, minimally invasive and available at an early stage of treatment, can help to individualize and guide treatment, avoid ineffective chemotherapies, provide near real-time analyses, and allow early detection in patients at risk for early relapse.

Thus, there remains a need to provide (among other things) new methods for the early assessment and prediction of the efficacy of cancer treatment regimens, in particular in patients undergoing therapy with a DNA-damaging chemotherapeutic agent.

The present disclosure seeks to address these and other needs in the art.

SUMMARY

In a first aspect, the present disclosure is directed to a method for predicting the efficacy of treatment with a chemotherapeutic agent such as a DNA-damaging chemotherapeutic agent in a patient diagnosed with cancer prior to commencement of treatment, i.e., pre-dose. More specifically, the method of the first aspect comprises determining the baseline expression level of one or more proteins, or any combination thereof, selected from the group consisting of topoisomerase I, RAD51, Ki-67, and ABCG2 in circulating tumor cells (CTCs) obtained from the patient prior to treatment with a DNA-damaging chemotherapeutic agent, to thereby predict the responsiveness of the tumor cells to treatment with the DNA-damaging chemotherapeutic agent. In the present context, it is understood that "prior to treatment" means prior to administering a given DNA damaging chemotherapeutic agent, and that the first aspect of the invention has applicability for patients experiencing both the first cycle and subsequent cycles of chemotherapy. For topoisomerase I, elevated CTC baseline expression levels indicate a predisposition to responsiveness to treatment with the DNA-damaging therapeutic agent and suppressed CTC baseline expression levels indicate a predisposition for unresponsiveness to treatment with the DNA-damaging therapeutic agent. Baseline expression levels of the various proteins, and a determination of whether a baseline expression level is elevated or suppressed is based upon a comparison to the mean and/or median baseline expression level of the protein in circulating tumor cells of the overall study population. For RAD51, elevated baseline expression levels indicate a predisposition for unresponsiveness to treatment with the DNA-damaging agent and suppressed baseline expression levels indicate a predisposition to responsiveness to treatment. For Ki-67, elevated baseline expression levels indicate a predisposition to responsiveness to treatment with the DNA-damaging therapeutic agent and suppressed baseline expression levels indicate a predisposition for unresponsiveness to treatment. For ABCG2, elevated baseline expression levels indicate a predisposition for unresponsiveness to treatment with the DNA-damaging agent and suppressed baseline expression levels indicate a predisposition to responsiveness to treatment.

In a second aspect, provided herein is a method for assessing the response of a patient diagnosed with cancer to treatment with a given chemotherapeutic agent, such as a DNA-damaging chemotherapeutic agent. The method comprises, for example, (i) determining the baseline expression level of one or more proteins selected from γ-H2Ax, RAD-51 and TUNEL, or any combination thereof, in circulating tumor cells obtained from the patient prior to treatment with the chemotherapeutic agent, (ii) treating the patient by administering a dosage amount of the DNA-damaging chemotherapeutic agent on a given dosing schedule, (iii) determining the expression level of the one or more proteins in circulating tumor cells obtained from the patient following said treating step, (iv) for the one or more proteins, comparing the expression level in step (iii) with the baseline expression level in step (i), wherein an increase in expression level is predictive of overall responsiveness to treatment with the DNA-damaging therapeutic agent and a decrease or no change in expression level is predictive of unresponsiveness to treatment.

In a third aspect, provided herein is a method for optimizing the therapeutic treatment regimen of a patient diagnosed with cancer, wherein the treatment regimen comprises administration of a chemotherapeutic agent such as a DNA-damaging chemotherapeutic agent. The method of the third aspect comprises the steps of (i) determining the baseline expression level of one or more proteins selected from topoisomerase I, RAD51, ABCG2, and topoisomerase II in circulating tumor cells obtained from the patient prior to treatment with the chemotherapeutic agent, (ii) treating the patient by administering a dosage amount of the DNA-damaging chemotherapeutic agent on a given dosing schedule, (iii) determining the expression level of the one or more proteins in circulating tumor cells obtained from the patient following said treating step, (iv) for the one or more proteins, comparing the expression level in step (iii) with the baseline expression level in step (i), (v) determining the resistivity or responsiveness of the patient to the treatment regimen by a method other than that of step (iv), (vi) in the event of resistivity of the patient to the treatment as determined in step (v), examining the change in expression level for said one or more proteins from step (iv), to thereby postulate a mechanism of action related to the resistivity of the patient to treatment, and (vii) based upon the postulation, developing a revised treatment regimen to include administration of one or more different chemotherapeutic agents that act on the tumor cells by a mechanism other than that postulated in step (vi) as being related to the development of resistivity, to thereby arrive at an improved therapeutic treatment regimen for the patient.

The method of the third aspect of the invention is based upon a comparison of the change in expression levels of the stated proteins with the efficacy of treatment, with an aim of determining how and why resistance occurs in certain patients. For instance, for the proteins Topoisomerase II, ABCG2, and RAD51, if resistance is observed in the patient, and expression levels are elevated for the protein, then this may indicate that the tumor will be responsive to inhibitors which target the upregulated protein itself or target the pathway in which the upregulated protein plays a role, thereby providing a guide to an alternative course of treatment.

Illustrative chemotherapeutic agents for use in the methods provided herein are DNA-damaging agents such as enzyme inhibitors, alkylating agents and intercalating agents. In one embodiment, the chemotherapeutic agent is a topoisomerase inhibitor. In yet an additional embodiment related to the foregoing, the chemotherapeutic agent is selected from camptothecin, irinotecan, topotecan, etoposide, SN-38 and poly(ethylene glycol)-modified versions of the foregoing. In a particular embodiment, the DNA-damaging therapeutic agent comprises SN-38 modified by releasable covalent attachment to one or more poly(ethylene glycol) polymers. In yet another embodiment, the DNA-damaging therapeutic agent comprises irinotecan modified by releasable covalent attachment to one or more poly (ethylene glycol) polymers (such as etirinotecan pegol). Illustrative and preferred DNA-damaging chemotherapeutic agents for use in the methods provided herein include etirinotecan pegol and tetrakis[(4S)-4,11-diethyl-9-hydroxy-3,14-dioxo-3,4,12,14-tetrahydro-1H-pyrano[3',4':6,7]indolizino[1,2-b]quinolin-4-yl]N,N',N",N"'-({α,α',α",α"'-[oxybis(propane-3,1,2-triyl)]tetrakis[poly(oxyethylene)]}tetrakis[oxy(1-oxo ethylene)])tetraglycinate.

Regarding any one or more of the methods described above, in one or more embodiments, the circulating tumor cells are obtained by immunomagnetic separation, membrane filtration, micro-electro-mechanical device, or dielectrophoresis field-flow fractionation. In a preferred embodiment, the circulating tumor cells are captured by dielectrophoresis field-flow fractionation.

Regarding any one or more of the methods provided above, in a preferred embodiment, the patient has breast cancer. In a more particular embodiment, the cancer is metastatic breast cancer.

In one or more of the foregoing aspects, baseline expression levels of the one or more proteins and the expression levels of the one or more proteins following treatment are determined based upon the percentage of positive cells and/or mean fluorescent intensity of the circulating tumor cells stained for detection of the one or more proteins.

Regarding the second or third aspects, in one embodiment, the determining step (iii) is carried out before the second cycle of treatment. In a particular embodiment, determining step (iii) is carried out within 21 days of administering a first dosage amount of the chemotherapeutic agent.

Regarding the second aspect, in one or more embodiments, steps (ii)-(iv) of the method are optionally repeated for 2-4 additional cycles. In yet a further embodiment of the foregoing, the cycle comprises administering the chemotherapeutic agent every 3 weeks.

Regarding the method of the second aspect of the invention, in a further embodiment, upon observation of a decrease in expression level of the one or more proteins in step (iv), either the dosage amount or dosing schedule in step (ii) or both are altered.

In yet another embodiment related to the method of the second aspect, upon observation of a decrease in expression level of the one or more proteins in step (iv), selection of the chemotherapeutic agent administered to the patient is altered.

In yet a further fourth aspect, provided herein is the use of the baseline expression level of one or more proteins in circulating tumor cells for predicting the efficacy of treatment with a chemotherapeutic agent, such as a DNA-damaging chemotherapeutic agent, in a patient diagnosed with cancer, wherein the one or more proteins are selected from the group consisting of topoisomerase I, RAD51, Ki-67, and ABCG2, and the circulating tumor cells are obtained from the patient prior to treatment.

In yet an additional fifth aspect, provided herein is the use of a comparison of baseline expression levels in circulating tumor cells of one or more proteins selected from γ-H2Ax, RAD-51 and TUNEL obtained from a patient diagnosed with cancer to expression levels of the one or more proteins in circulating tumor cells obtained from the patient after treatment with a chemotherapeutic agent such as a DNA-damaging chemotherapeutic agent, wherein the baseline expression levels are determined prior to treatment with the chemotherapeutic agent, and for the one or more proteins, an increase in expression level after treatment is predictive of overall responsiveness to treatment and a decrease in expression level is predictive of unresponsiveness to treatment.

In a preferred embodiment related to the foregoing uses, the cancer is metastatic breast cancer and the DNA-damaging chemotherapeutic agent is etirinotecan pegol.

Each of the herein-described features of the invention is meant to apply equally to each and every embodiment as described herein, unless otherwise indicated.

Additional embodiments of the invention are set forth in the following description and claims.

BRIEF DESCRIPTION OF THE FIGURES

FIG. 1 is a schematic diagram of the ApoStream™ device (taken from Gupta et al., *Biomicrofluidics* 6, 024133 (2012)) for antibody independent isolation and recovery of viable cancer cells from blood (circulating tumor cells), where the inset shows cell flow and separation in the flow chamber. See, e.g., Example 5.

DETAILED DESCRIPTION

Definitions

In describing and claiming the present invention, the following terminology will be used in accordance with the definitions described below.

As used in this specification, the singular forms "a," "an," and "the" include plural referents unless the context clearly dictates otherwise.

The phrase, "combinations thereof" as used herein refers to all permutations and combinations of the listed items preceding the phrase. For example, "A, B, C, and combinations thereof" is intended to include A, B, C, AB, AC, BC, and ABC, and if order is relevant, to also include BA, CA, CB, CBA, BCA, ACB, BAC and CAB.

"Biomarker" or "biological marker", is in general a substance used as an indicator of a biological state. A biomarker is objectively measured and can be evaluated as an indicator of a biological process, pathogenic process or pharmacologic response to therapeutic intervention.

A "DNA-damaging agent" is a chemotherapeutic agent, sometimes referred to as a genotoxic agent, that affects nucleic acids and alters their function. These agents may directly bind to DNA or they may indirectly lead to DNA damage by affecting enzymes involved in DNA replication. General classes of DNA-damaging agents include alkylating agents, intercalating agents and enzyme inhibitors. A compound considered to be a DNA-damaging agent may also possess other mechanisms of action.

"Statistically significant" differences between groups relates to values, such that when using the appropriate statistical analysis, the probability of the groups being the same is less than 5% (e.g., p<0.05). That is to say, the probability of obtaining the same results on a completely random sample is less than 5 out of 100 attempts.

"Baseline expression level" as used herein refers to the expression level of a given protein in circulating tumor cells (CTCs) obtained from a patient prior to treatment with a chemotherapeutic agent of interest (which does not preclude prior treatment of the patient under a prior treatment regimen). The baseline expression level is compared to the mean or median baseline expression level of the same protein in CTCs of the overall study population as determined by appropriate statistical analysis or is based on the application of other adequate statistical methodologies to define sensitive and specific cutoff values.

"Percent positive CTCs" for a given biomarker provide one measure of chemotherapeutic response and refers to the percentage of CTCs in which the given biomarker is detected from the same cells reported in the total CTC count.

A treatment "cycle" of a patient undergoing chemotherapy refers to the administration of a dosage of a particular drug or combination of drugs over a duration of time (which can be minutes, hours, or even days depending upon the protocol), followed by an interval of time in which no drug is administered. Chemotherapy treatment may repeat weekly, biweekly, every three weeks, monthly, bimonthly, etc., where each administration followed by an interval of time in which no drug is administered is referred to as a "cycle". A chemotherapeutic treatment regimen may consist of 1 or more cycles, and may also include chemotherapy which extends for a period of time beyond an assessment of the patient being cancer-free.

"PEG" or "polyethylene glycol," as used herein, is meant to encompass any water-soluble poly(ethylene oxide). Unless otherwise indicated, a "PEG polymer" or a polyethylene glycol is one in which substantially all (preferably all) monomeric subunits are ethylene oxide subunits, though, the polymer may contain distinct end capping moieties or functional groups, e.g., for conjugation. PEG polymers for use in the present invention will comprise one of the two following structures: "—$(CH_2CH_2O)_n$—" or "—$(CH_2CH_2O)_{n-1}$$CH_2CH_2$—," depending upon whether or not the terminal oxygen(s) has been displaced, e.g., during a synthetic transformation. The variable (n) can range from about 3 to 4000, and the terminal groups and architecture of the overall PEG can vary.

"Branched," in reference to the geometry or overall structure of a polymer, refers to a polymer having two or more polymer "arms" extending from a branch point.

A "physiologically cleavable" or "hydrolyzable" or "degradable" or "releasable" bond is a relatively labile bond that reacts with water (i.e., is hydrolyzed) under physiological conditions. The tendency of a bond to hydrolyze in water may depend not only on the general type of linkage connecting two atoms within a given molecule but also on the substituents attached to these atoms. Appropriate hydrolytically unstable or weak linkages include but are not limited to carboxylate ester, phosphate ester, anhydrides, acetals, ketals, acyloxyalkyl ether, imines, orthoesters, peptides, oligonucleotides, thioesters, and carbonates.

An "enzymatically degradable linkage" means a linkage that is subject to degradation by one or more enzymes.

A "stable" linkage or bond refers to a chemical bond that is substantially stable in water, that is to say, does not undergo hydrolysis under physiological conditions to any appreciable extent over an extended period of time. Examples of hydrolytically stable linkages include but are not limited to the following: carbon-carbon bonds (e.g., in aliphatic chains), ethers, amides, amines, and the like. Generally, a stable linkage is one that exhibits a rate of hydrolysis of less than about 1-2% per day under physiological conditions. Hydrolysis rates of representative chemical bonds can be found in most standard chemistry textbooks.

"Etirinotecan Pegol" (synonyms include pentaerythritolyl-4-arm-(polyethylene glycol-1-methylene-2-oxo-vinylamino acetate-linked-irinotecan; and poly(oxy-1,2-ethanediyl), α-hydro-ω-[2-[[2-[[(4S)-9-[([1,4'-bipiperidin]-1'-ylcarbonyl)oxy]-4,11-diethyl-3,4,12,14-tetrahydro-3,14-dioxo-1H-pyrano[3',4':6,7]indolizino[1,2-b]quinolin-4-yl]oxy]-2-oxoethyl]amino]-2-oxoethoxy]-, ether with 2,2-bis(hydroxymethyl)-1,3-propanediol (4:1); and tetrakis{(4S)-9-[([1,4'-bipiperidinyl]-1'-carbonyl)oxy]-4,11-diethyl-3,14-dioxo-3,4,12,14-tetrahydro-1H-pyrano[3',4':6,7]indolizino[1,2-b]quinolin-4-yl}N,N',N'',N'''-{methanetetrayltetrakis[methylenepoly(oxyethylene)oxy(1-oxoethylene)]} tetraglycinate, CAS Registry No. 848779-32-8, possesses the following structural formula:

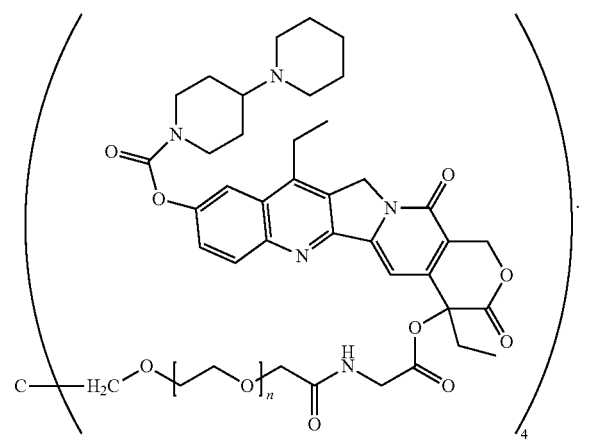

"Substantially" or "essentially" means nearly totally or completely, for instance, 95% or greater, more preferably 97% or greater, still more preferably 98% or greater, even more preferably 99% or greater, yet still more preferably 99.9% or greater, with 99.99% or greater being most preferred of some given quantity.

"Pharmaceutically acceptable excipient" or "pharmaceutically acceptable carrier" refers to a component that may be included in the compositions provided herein and causes no significant adverse toxicological effects to a patient.

The term "patient," refers to a living organism suffering from or prone to a condition that can be prevented or treated by a particular therapeutic regimen, and includes both humans and animals.

Overview

Described herein are proteins discovered to be useful as pharmacodynamic biomarkers. The proteins are detectable in circulating tumor cells in the peripheral blood of cancer patients, and methods have been developed to utilize changes in the expression levels of such proteins to predict and monitor a patient's response to therapy with a given chemotherapeutic agent. Certain proteins were discovered to be useful as baseline markers (markers predictive of a patient's response to therapy prior to treatment), while other markers (with some overlap) were found likely to be useful in monitoring a patient's response to therapy, in nearly real time. As a result, provided herein are methods directed to the prediction and early assessment of the efficacy of cancer treatment regimens, in particular in patients undergoing therapy with a DNA-damaging chemotherapeutic agent such as etirinotecan pegol or its active metabolite upon administration, SN-38.

As can be seen from the supporting examples (Examples 1-5), screening was carried out to identify optimal biomarkers detectable in circulating tumor cells, where certain preferred biomarkers for use in the methods described herein were found to possess a certain robustness, and further exhibited a sizable degree of change in expression level upon exposure to one or more illustrative chemotherapeutic agents. In preliminary screening experiments, a number of biomarkers were explored in various cancer cell lines as well as in PBMCs, to investigate the response of the potential markers ex vivo to exemplary chemotherapeutic agents.

Additionally, CTCs isolated from patient blood samples were analyzed prior to chemotherapeutic treatment, to further identify biomarkers for use as baseline biomarkers for predicting a patient's response to treatment prior to commencement of chemotherapy, and to identify biomarkers useful for predicting patient responsivity to treatment over the course of chemotherapy (i.e., treatment-suitable biomarkers). These and other aspects of the invention will now be more fully described below.

CTC Recovery from Blood

The methods provided herein involve determining expression levels of one or more proteins discovered to be useful as predictive, pharmacodynamic biomarkers in circulating tumor cells obtained from a patient having cancer.

Circulating tumor cells are rare cells present in the blood in numbers as low as one CTC per $10^6$-$10^7$ leukocytes. Circulating tumor cells have been isolated in the peripheral blood samples of patients with various kinds of malignancies such as metastatic breast, prostate, and colorectal cancer, and elevated CTC numbers have been found to correlate, in certain instances, with adverse clinical outcomes (Pantel, K., and Alix-Panabieres, C., Nat. *Clin. Pract. Oncol.*, 4, 62-63 (2007)). In contrast to the above, the instant disclosure relies upon the use of certain biomarkers, and in particular, the changes in expression of specific markers on circulating tumor cells, for predicting the outcome of treatment, either prior to or during treatment, with a particular chemotherapeutic agent, e.g., a DNA-damaging agent.

For use in the methods provided herein, circulating tumor cells can be isolated by a any of a number of different techniques. These techniques include immunomagnetic separation, membrane filtration, and microelectro-mechanical system (MEMS) chips.

Immunomagnetic separation relies on the expression of known cell surface markers such as the epithelial cell adhesion molecule or EpCAM. CTCs can be captured and isolated using the CellSearch® system, a CTC system for enumerating circulating tumor cells of epithelial origin by immunomagnetic separation techniques. The CellSearch® system is available at many laboratories (e.g., Quest Diagnostics, Genopix Medical Laboratory, etc.).

Circulating tumor cells can also be isolated, quantified and analyzed using membrane filtration techniques. A device which utilizes such an approach is the ScreenCell® mini-device in which CTCs are isolated from blood by size-selective isolation (Cayre, Y. E., *Anticancer Research*, 31 (2), 2011, 427-441).

Alternatively, circulating tumor cells may also be obtained by use of a microfluidic platform (i.e., 'CTC-ichip') capable of separation of viable CTCs from peripheral whole blood samples (See, e.g., Nagrath, S., *Nature*, 450 (7173), 2007, 1235-1239; Ozkumur, E., et al., *Sci Transl Med* 3, April 2013: 5 (3), 179). The separation is mediated by the interaction of target CTCs with antibody (EpCAM)-coated microposts under controlled laminar flow conditions.

In a preferred embodiment, circulating tumor cells are isolated using dielectrophoretic field flow fractionation technology such as provided by use of an ApoStream™ device as described in detail in Gupta, V., et al., 2012 (ibid). See, e.g., Example 5 herein. The ApoStream™ device utilizes continuous flow technology for the isolation and enrichment of CTCs from whole blood as illustrated in FIG. 1. Briefly, the flow chamber applies an AC electric field to the sample within a defined region of the flow path. A flexible polyimide film sheet with electroplated copper and gold electrodes forms the floor of the flow chamber, an acrylic sheet forms the ceiling, and a gasket forms the side walls of the chamber. Eluate buffer is introduced at the upstream end of the flow chamber. The sample is introduced through a port located downstream from the sample inlet port. When cells encounter the DEP (dielectrophoretic) field, the DEP forces pull cancer cells towards the chamber floor and repel other cells as they traverse the electrode. Cancer cells travelling close to the chamber floor are withdrawn through the collection port, while other blood cells travelling at greater heights are carried beyond the port and exit the chamber to the waste container via a second outlet port.

Chemotherapeutic Agents

The methods provide herein are directed to treating a patient diagnosed with cancer with one or more chemotherapeutic agents. Generally, a single chemotherapeutic agent is administered, however, in some cases, if warranted, combination therapy with administration of one or more additional chemotherapeutic agents may be employed. Most typically, combination therapy, if used, involves the administration of two different chemotherapeutic agents, where, in certain instances, each chemotherapeutic agent will possess a different mechanism of action. Reference to any one or more chemotherapeutic agents as provided herein is meant to also encompass pharmaceutically acceptable salts and solvates thereof, as applicable. See, e.g., P. H. Stahl and C. G. Wermuth, editors, *Handbook of Pharmaceutical Salts: Properties, Selection and Use*, Weinheim/Zürich: Wiley-VCH/HCA, 2002.

Preferably, although not necessarily, the chemotherapeutic agent is a DNA-damaging agent. Illustrative DNA-damaging agents include the platins such as cis-platin, carboplatin and oxiplatin, each of which acts as a DNA-crosslinker. Another DNA-damaging agent, methotrexate, useful for the methods described herein, functions by preventing DNA synthesis by inhibiting dihydrofolate reductase (DHFR).

Additional chemotherapeutic agents include the antimetabolites. The antimetabolites represent a class of anticancer drugs that mimic normal cellular molecules and consequently interfere with DNA replication. Many of these compounds are DNA antagonists that exert their activity by blocking nucleotide metabolism pathways. Examples of antimetabolite compounds include the pyrimidine analogs 5-fluorouracil (5-FU), capecitabine, floxuridine, and gemcitabine, and the purine analogs 6-mercaptopurine, 8-azaguanine, fludarabine, and cladribine.

Further DNA-damaging chemotherapeutic agents include enzyme inhibitors such as the topoisomerase inhibitors. Topoisomerases are a class of enzymes responsible for releasing the torsional strain of the DNA double helix. Topoisomerase I allows the passage of a single DNA strand through a transient single-strand break created in the complementary strand of the double helix. Topoisomerase II cuts both strands of the double helix to allow the passage of an intact helix to unwind supercoiled DNA. Topoisomerase inhibitors trap the DNA-enzyme intermediate as a complex, preventing re-ligation of the break, inhibiting replication fork progression, and causing toxic DSBs (Froelich-Ammon and Osheroff, *J. Biol. Chem.* 270, 1995, 21429-21432). Preferred for use in the methods provided herein are the topoisomerase-I inhibitors. Exemplary chemotherapeutics possessing this mechanism of action include camptothecin, 10-hydroxycamptothecin, 11-hydroxycamptothecin, topotecan, irinotecan, and SN-38, the active metabolite of irinotecan. Additional DNA-damaging agents include the topoisomerase II-inhibitors, etoposide, doxorubicin and daunorubicin.

In one or more embodiments, the chemotherapeutic agent is covalently attached to one or more water-soluble polymers such as poly(ethylene glycol) or PEG. Such agents are generally referred to as "PEGylated". The covalent attachment between the poly(ethylene glycol) and the chemotherapeutic agent may be stable or releasable in nature, and may be direct or via an intervening spacer or linker. The poly(ethylene glycol) moiety may possess any of a number of different geometries, for example, linear, branched, or multi-armed.

In a preferred embodiment, the chemotherapeutic agent is a topoisomerase I inhibitor such as irinotecan, topotecan, camptothecin, or SN-38, modified by releasable covalent attachment to one or more water-soluble polymers such as poly(ethylene glycol). Illustrative releasable linkages include carboxylate ester, phosphate ester, anhydride, acetal, ketal, acyloxyalkyl ether, imine, orthoester, peptide and oligonucleotide. In a preferred embodiment, the releasable linkage is a carboxylate ester.

Exemplary and non-limiting examples of such chemotherapeutic compounds are encompassed by the following formula: $C[CH_2-O-(CH_2CH_2O)_n-CH_2\text{-Term}]_4$, wherein n, in each instance, is an integer having a value from 5 to 150 (e.g., about 113); and Term, in each instance, is selected from the group consisting of —OH, —C(O)OH,

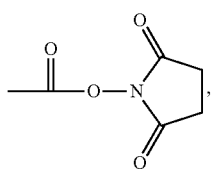

and —NH—CH$_2$—C(O)—O-Irino, wherein Irino is a residue of irinotecan, and, in a composition of such compounds, at least 90% are Irino and the remaining 10% are selected from the group consisting of —OH, —C(O)OH,

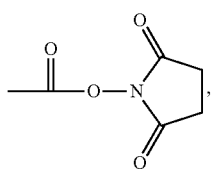

and pharmaceutically acceptable salts (included mixed salts) thereof. Preferably, the irinotecan is modified at its 10-, 11- or 20-ring position. These and other compounds and compositions are described in International Patent Publication No. WO 2011/063156.

Additional exemplary and non-limiting examples of poly (ethylene glycol)-modified topoisomerase I inhibitors include compounds encompassed by the following formula:

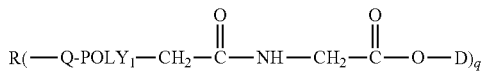

where R is an organic radical possessing from 3 to 150 carbon atoms, Q is a linker, wherein R, when taken together with Q to form $R(\text{-Q-})_q$, is a residue of a polyol or a polythiol after removal of "q" hydroxyl or thiol protons, respectively to form a point of attachment for POLY$_1$, POLY$_1$ poly (ethylene glycol), D is a camptothecin attached at its 10-, 11- or 20-ring position, and q has a value from 3 to 50, and pharmaceutically acceptable salts (included mixed salts) thereof.

For example, the following pentaerythritol-based multi-arm structures are preferred topoisomerase I inhibitors:

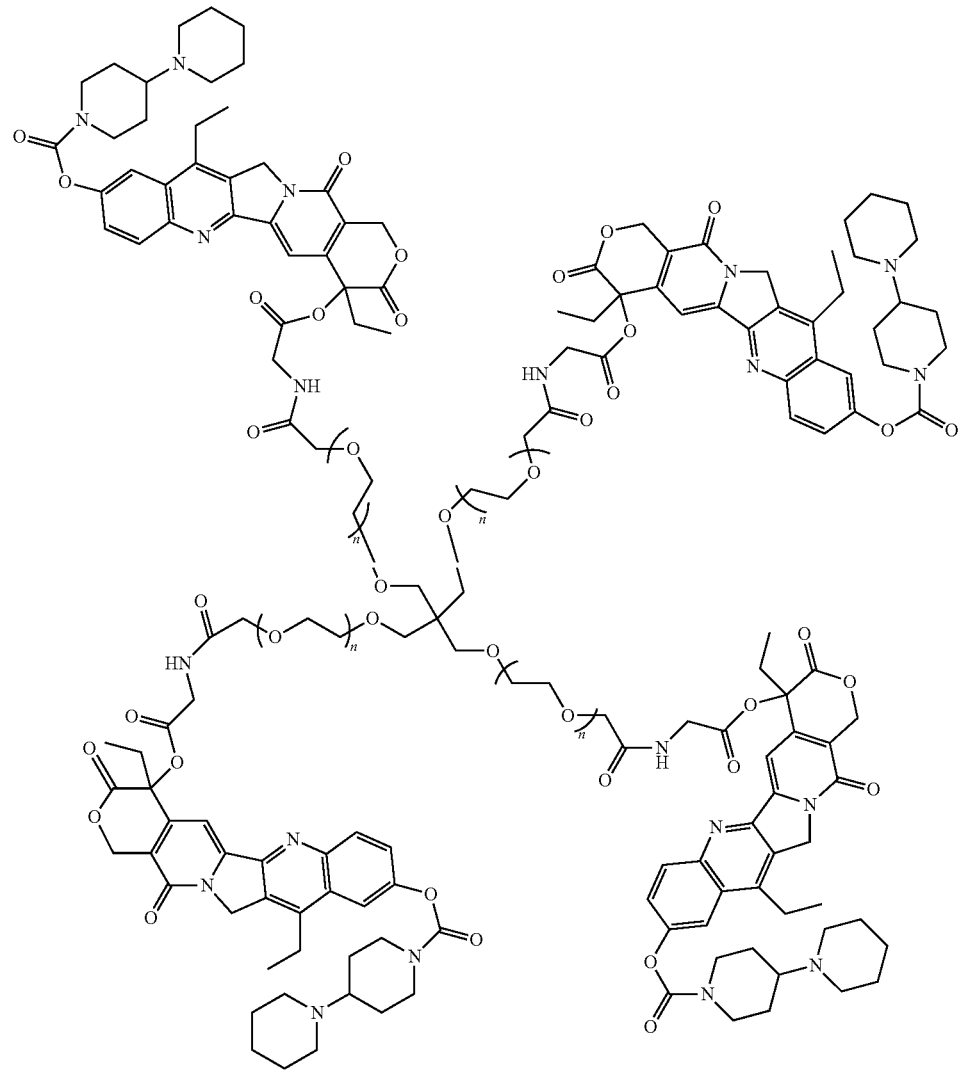

wherein each n is an integer ranging from 40 to about 500 (e.g., about 113 and about 226), and pharmaceutically acceptable salts (included mixed salts) thereof. The above and other compounds are described in U.S. Pat. No. 7,744,861, and are considered "pentaerythritol-based multi-arm polymer conjugates of irinotecan" or a "PBMAPCI."

Further additional polymer-modified topoisomerase I inhibitors include compounds encompassed by the following formula

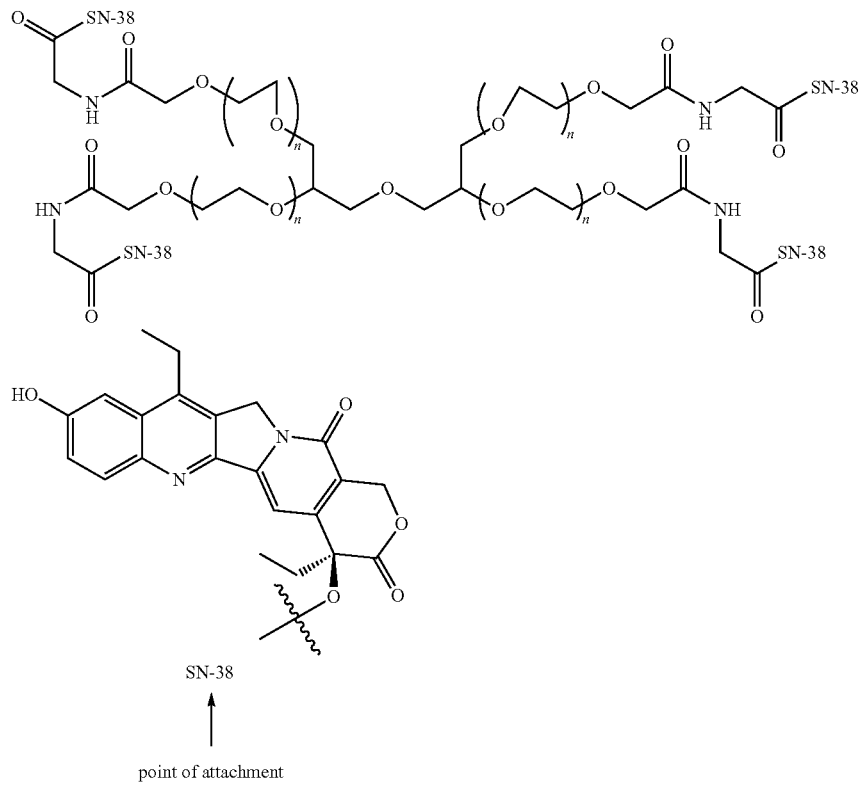

point of attachment wherein each (n) is a positive integer from about 28 to about 341 and each SN38 is a residue of SN-38. These and other compounds are described in WO 2007/092646, Sapra et al. Abstract 145 entitled "Marked therapeutic efficacy of a novel poly(ethylene-glycol) conjugated SN38 conjugate in xenograft models of breast and colorectal cancers," Patnaik et al. (2009) Poster C221 presented at AACR-NCI-EORTC.

Generally, the weight-average molecular weight of the poly(ethylene glycol) in the modified chemotherapeutic agent is from about 100 Daltons to about 150,000 Daltons. Exemplary ranges, however, include weight-average molecular weights in the range of 2,000 daltons to about 100,000 daltons, or from about 3,000 daltons to about 70,000 daltons, or in the range of from about 5,000 daltons to about 60,000 daltons. Overall weight-average molecular weights of the poly(ethylene glycol)-modified chemotherapeutic include about 500 daltons, about 600 daltons, about 700 daltons, about 750 daltons, about 800 daltons, about 900 daltons, about 1,000 daltons, about 1,500 daltons, about 2,000 daltons, about 2,200 daltons, about 2,500 daltons, about 3,000 daltons, about 4,000 daltons, about 4,500 daltons, about 5,000 daltons, about 5,500 daltons, about 6,000 daltons, about 7,000 daltons, about 7,500 daltons, about 10,000 daltons, about 12,000 daltons, about 15,000 daltons, about 20,000 daltons, about 22,500 daltons, about 25,000 daltons, about 30,000 daltons, about 35,000 daltons, about 40,000 daltons, about 45,000 daltons, about 50,000 daltons, about 55,000 daltons, about 60,000 daltons, about 65,000 daltons, about 70,000 daltons, and about 75,000 daltons. Preferred overall weight-average molecular weights of a poly(ethylene glycol)-modified chemotherapeutic include 15,000 daltons, 20,000 daltons, and 40,000 daltons.

In one or more particular embodiments related to the herein described methods and uses, the DNA-damaging chemotherapeutic agent is etirinotecan pegol. In yet another preferred embodiment, the chemotherapeutic compound is firtecan pegol (also known as EZN-2208 or tetrakis[(4S)-4,11-diethyl-9-hydroxy-3,14-dioxo-3,4,12,14-tetrahydro-1H-pyrano[3',4':6,7]indolizino[1,2-b]quinolin-4-yl]N,N',N'',N'''-({α,α',α'',α'''-[oxybis(propane-3,1,2-triyl)]tetrakis[poly(oxyethylene)]}tetrakis[oxy(1-oxoethylene)]) tetraglycinate).

Proteins Useful as Biomarkers

As can be seen from the accompanying illustrative examples, proteins useful as pharmacodyamic biomarkers have been identified, quantified and evaluated in both representative cancer cell lines and in CTCs obtained from metastatic breast cancer patients. Proteins discovered to have utility as baseline expression biomarkers on CTCs for predicting the responsiveness of a patient to treatment with a given DNA-damaging chemotherapeutic agent include topoisomerase I (TOP1), RAD51, Ki-67, and ABCG2, and combinations thereof. See, e.g., Example 5. Such information can be extremely useful for optimizing treatment by selecting (or excluding) patients for treatment with a particular chemotherapeutic agent as illustrated herein, e.g., etirinotecan pegol.

One of the proteins identified as having utility as a pre-treatment biomarker is topoisomerase I. Topoisomerases are enzymes that regulate the overwinding or underwinding of DNA, and their activity can impact downstream cell replication and death. Topoisomerase catalyzes the transient breaking and rejoining of a single strand of DNA which allows the strands to pass through one another, thus altering the topology of DNA. Inhibition of topoisomerase causes single and double strand breaks to occur in the cellular DNA, leading to apoptosis. In examining the expression levels of topoisomerase I in CTCs from a patient having cancer prior to treatment with a DNA-damaging chemotherapeutic agent, it has been found that elevated baseline expression levels in CTCs indicate a predisposition to responsiveness to treatment with the DNA-damaging therapeutic agent, while suppressed baseline expression levels indicate a predisposition for unresponsiveness or resistance to treatment with the DNA-damaging therapeutic agent.

Yet another pre-dose marker found to be particularly predictive in CTCs is RAD-51. RAD-51 plays a major role in DNA damage repair by contributing to homologous recombination of DNA during double strand break repair. It has been discovered that in examining CTCs obtained from a patient prior to treatment with a DNA-damaging agent such as irinotecan, SN-38 or PEGylated forms thereof, elevated baseline expression levels of RAD-51 on the CTCs indicate a predisposition for unresponsiveness to treatment with the DNA-damaging agent, while suppressed baseline expression levels indicate a predisposition to responsiveness to treatment.

A further protein found to be predictive of responsivity of a patient to treatment with a DNA-damaging agent in CTCs is Ki-67, a marker for cellular proliferation. Ki-67 expression is localized in the nucleus during all active phases of the cell cycle, but is absent in non-proliferating cells. It has been discovered that elevated baseline expression levels of Ki-67 indicate a predisposition to responsiveness to treatment with the DNA-damaging therapeutic agent such as those provided herein and suppressed baseline expression levels indicate a predisposition for unresponsiveness to treatment.

An additional protein, ABCG2 or ATP-binding cassette sub-family G member 2, has similarly been discovered to have utility as a pre-dose biomarker in CTCs obtained from a patient with cancer. ABCG2 is a membrane associated protein responsible for transporting various molecules across extra- and intra-cellular membranes. It has been discovered that elevated baseline expression levels of ABCG2 appear to indicate a predisposition for unresponsiveness to treatment with the DNA-damaging agent and suppressed baseline expression levels indicate a predisposition to responsiveness to treatment.

In assessing the change in baseline expression level for a given protein, the baseline expression level is compared to the mean or median baseline expression level of the same protein in CTCs of the overall study population as determined by appropriate statistical analysis or is based on the application of other adequate statistical methodologies to define sensitive and specific cutoff values. To be indicative of a predisposition for responsiveness or unresponsiveness to treatment, the magnitude of change in expression level (either elevated or suppressed) should ideally be at least 10%, or preferably at least 20%, or even more preferably 25% or greater, when compared to the mean or median baseline expression level of the protein in CTCS of the overall study population. In one embodiment directed to any one or more of the pre-dose CTC biomarkers described above, the magnitude of change in expression level is minimally at least 10%. In yet a further embodiment, the magnitude of change in expression level is minimally at least 20%. In yet a further embodiment, the magnitude of change in expression level is at least 30%. In yet a further embodiment, the magnitude of change in expression level is at least 40%.

In addition to the pre-dose markers described above, certain post-dose biomarkers have been identified. Proteins discovered to possess utility as CTC-biomarkers for assessing the response of a cancer patient to treatment with a chemotherapeutic agent over the course of chemotherapy include γ-H2Ax, RAD-51 and TUNEL, or any combination thereof.

RAD-51 is described above, and is herein noted to be advantageous as both as pre-dose and a post-dose CTC biomarker for use in the instant methods, among others.

Yet an additional pharmacodynamics biomarker has been discovered for post-dosage use in predicting patient response to therapy in CTCs, phosphorylated H2AX (γ-H2Ax). γ-H2Ax is a marker of DNA-double strand break damage. Following DSB damage, the ataxia telangiectasia-mutated (ATM) protein kinase becomes activated and initiates a signal transduction pathway mobilizing DNA damage repair proteins. Phosphorylation of H2AX is one of the first steps in recruiting DNA-repair complexes to the site of DSBs.

A further predictive indicator of a patient's response to chemotherapy following commencement of dosing is terminal deoxynucleotidyl transferase dUTP nick end labeling (TUNEL). TUNEL is a method for detecting DNA fragmentation that results from apoptotic signaling cascades by labeling the terminal end of nucleic acids. The assay relies on the presence of nicks in the DNA which can be identified by terminal deoxynucleotidyl transferase (TdT).

For the foregoing, i.e., RAD-51, γ-H2Ax, and TUNEL, an increase in expression level over baseline is predictive of overall responsiveness to treatment with the DNA-damaging therapeutic agent, e.g., etirinotecan pegol, and a decrease or no change in expression level is predictive of unresponsiveness to treatment. To be predictive of a predisposition for responsiveness to treatment, the increase in expression level for a given marker or markers in individual patient CTCs over baseline should ideally be at least 10%, or preferably at least 20%, or even more preferably 25% or greater. An observation of up-regulation of more than one of RAD-51, γ-H2Ax, and TUNEL provides an even stronger correlation and prediction of a positive response of the patient to treatment with a given chemotherapeutic. In yet a further embodiment, the increase in expression level is at least 30%. In yet a further embodiment, the increase in expression level is at least 40%. In yet another embodiment, the increase in expression level is at least 50% or more. In certain instances, the expression levels may increase by at least about 60%, 70%, 80%, 90% or 100% or more. This approach may allow clinicians to more quickly optimize therapeutic regimens, optimize dosage amounts to increase efficacy while minimizing toxicities, etc. CTCs may be collected at various time-points post-administration of the DNA-damaging agent. Blood samples may be collected at a number of hours post-dosing (1 hour, 2 hours, 8 hours, 12 hours, 24 hours) or days post-dosing (2 days, 3 days, 5 days, 7 days, 10 days, 15 days, 20 days), or 1 or 2 weeks post-dose. That is to say, samples may be collected at any time post-dose and prior to a second cycle of chemotherapy treatment. Tumor biopsies may also be examined to determine and correlate expression levels of the various post-treatment biomarkers in the biopsy samples against those found in the CTCs. The foregoing may also allow clinicians to determine optimum dosages and schedules for treatment. Moreover, for combination therapies, the foregoing may allow clinicians to optimize the therapeutic ratio between tumor cell death and toxicity.

Additionally, expression levels of the proteins, topoisomerase I, RAD51, ABCG2, and topoisomerase II, may be examined in CTCs obtained from a cancer patient over the course of treatment, as in the foregoing, and compared to baseline levels of the same, to thereby gain additional insights into the various mechanisms of action of the chemotherapeutic agent on the patient contributing to resistance to treatment. This information is then used to develop a revised and improved treatment regimen to include administration of one or more different chemotherapeutic agents that act on the tumor cells by a mechanism other than that postulated as being related to the development of resistivity based upon the change in expression levels observed in the CTCs. For each of topoisomerase II, ABCG2, and RAD51, if resistance is observed in the patient, and expression levels are elevated for the particular protein, then this may indicate that the tumor will be responsive to inhibitors which target the upregulated protein itself or target the pathway in which the upregulated protein plays a role, thereby providing a guide to an alternative course of treatment.

Expression levels of the foregoing proteins in CTCs may be measured in terms of percent positive cells (i.e., the percentage of CTCs positive for the particular protein) and mean fluorescence intensity (MFI) determined by laser scanning cytometry as described in detail in the accompanying examples. Captured CTCs may, for example, be labeled with a fluorescent dye such as CellTracker™ dye or any other appropriate dye, and then visualized by fluorescence microscope.

Method

The methods described herein involve the administration of a chemotherapeutic agent, preferably a DNA-damaging agent, for treatment of a patient having cancer. Preferably, the DNA-damaging agent is a topoisomerase I inhibitor such as campothecin, irinotecan, SN-38, topotecan or a poly(ethylene glycol)-modified form thereof such as pentaerythritolyl-4-arm-(polyethyleneglycol-1-methylene-2 oxo-vinylamino acetate-linked—irinotecan)-20 kD.

Prior to commencement of treatment, a blood sample is obtained from the patient from which CTCs are obtained and analyzed to provide baseline levels of certain biomarkers as described herein. The chemotherapeutic agent is administered to a patient on a given dosing schedule over a duration of time in a therapeutically effective amount. One of ordinary skill in the art can determine an appropriate initial patient treatment regimen, i.e., chemotherapeutic agent, dosage amount, schedule, and the like, based upon information available in the literature, when taken into consideration of the patient's condition.

For administration of a topoisomerase I-inhibitor, particularly with respect to a pentaerythritol-based multi-arm polymer conjugate of irinotecan, such as etirinotecan pegol, a therapeutically effective amount is an amount encompassed by one or more of the following ranges: from about 1 mg/m$^2$ to about 1000 mg/m$^2$ of body surface; from about 2 mg/m$^2$ to about 900 mg/m$^2$ of body surface; from about 3 mg/m$^2$ to about 800 mg/m$^2$ of body surface; from about 4 mg/m$^2$ to about 700 mg/m$^2$ of body surface; from about 5 mg/m$^2$ to about 600 mg/m$^2$ of body surface; from about 6 mg/m$^2$ to about 550 mg/m$^2$ of body surface; from about 7 mg/m$^2$ to about 500 mg/m$^2$ of body surface; from about 8 mg/m$^2$ to about 450 mg/m$^2$ of body surface; from about 9 mg/m$^2$ to about 400 mg/m$^2$ of body surface; from about 10 mg/m$^2$ to about 350 mg/m$^2$ of body surface; from about 20 mg/m$^2$ to about 200 mg/m$^2$ of body surface; from about 30 mg/m$^2$ to about 200 mg/m$^2$ of body surface; from about 40 mg/m$^2$ to about 270 mg/m$^2$ of body surface; and from about 50 mg/m$^2$ to about 240 mg/m$^2$ of body surface.

The actual dose to be administered will vary depend upon the age, weight, and general condition of the subject as well as the severity of the condition being treated, the judgment of the health care professional, and particular chemotherapeutic compound being administered, particularly in view of its related toxicity.

The dosage of any given chemotherapeutic agent can be administered in a variety of dosing schedules depending on the judgment of the clinician, needs of the patient, and so forth. The specific dosing schedule will be known by those of ordinary skill in the art or can be determined experimentally using routine methodologies. Exemplary dosing schedules include, without limitation, administration five times a day, four times a day, three times a day, twice daily, once daily, three times weekly, twice weekly, once weekly, twice monthly, once monthly, and any combination thereof. For instance, the dosing schedule may include administration every 7 days, every 10 days, every 14 days, every 21 days, and so forth. Chemotherapy treatment occurs in cycles, with each period of treatment followed by a recovery period. A treatment regimen may include one cycle, 2, cycles, 3 cycles, 4 cycles or even more if deemed necessary based upon patient response. Once the clinical endpoint has been achieved, chemotherapy is halted. An exemplary dosing schedule for etirinotecan pegol in metastatic breast cancer patients is 145 mg/m$^2$ every 14 days (q14d) or every 21 days (q21d). See Example 6. Typically, the duration of treatment, including multiple cycles, extends over months, e.g., for at least 6 weeks, for at least 8 weeks, for at least 12 weeks, for at least 16 weeks, and so forth.

Following administration of the chemotherapeutic agent, a blood sample is taken from the patient, CTCs are isolated as previously described, and analyzed to determine expression levels of the various biomarkers described in detail above. For example, blood samples may be collected at a number of hours post-dosing (1 hour, 2 hours, 8 hours, 12 hours, 24 hours) or days post-dosing (2 days, 3 days, 5 days, 7 days, 10 days, 15 days, 20 days), or 1 or 2 weeks post-dose. That is to say, samples may be collected at any time post-dose and prior to a second round of treatment. The level of the marker post-initial dose can be determined at any day following the initial dosing, although it is preferred to take the first post-dosing tumor marker level at least 3-14 days following administration (e.g., 3, 4, 5, 6, 7, 8. 9, 10, 11, 12, 13, or 14 days), in particular for poly(ethylene glycol)-modified chemotherapeutic agents, due to their long-acting nature, to allow the compound sufficient time to exert a therapeutic and measurable effect on the CTC marker. Over the course of treatment, one or more additional CTC post-dose marker determinations can be carried out. For example, CTC post-dose marker levels can be determined at 1 week, 2 weeks, 3 weeks following administration of the initial dose, and through multiple cycles of treatment, depending upon the recovery period employed. Additionally, more than one CTC post-dose marker determination can be conducted in one cycle (e.g., at 5 days post-dose, at 10 days post dose, and at 21 days post-dose, or at any day or combination of days in the rest period) prior to administration of the chemotherapeutic agent in a second cycle of chemotherapy.

While administration of the chemotherapeutic agent is generally via a parenteral route, other modes of administration are also contemplated, such as pulmonary, nasal, buccal, rectal, sublingual, and transdermal. As used herein, the term "parenteral" includes subcutaneous, intravenous, intra-arterial, intraperitoneal, intracardiac, intrathecal, and intramuscular injection, as well as infusion injections.

The methods herein described may be applied to treatment of a number of cancers. Exemplary cancers include fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell cancer, basal cell cancer, adenocarcinoma, sweat gland cancer, sebaceous gland cancer, papillary cancer, papillary adenocarcinomas, cystadenocarcinoma, medullary cancer, bronchogenic cancer, renal cell cancer, hepatoma, bile duct cancer, choriocarcinoma, seminoma, embryonal cancer, Wilms' tumor, cervical cancer, testicular cancer, lung cancer, small cell lung cancer, bladder cancer, epithelial cancer, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma and leukemias. Preferably, the cancer is a solid tumor. Most generally, the patient is one diagnosed with colon, lung, or breast cancer.

In reference to a patient diagnosed with breast cancer, the patient treated in accordance with the methods described herein may possess any of a number of types of breast cancer, including ductal carcinoma in situ, invasive ductal carcinoma, triple negative breast cancer, inflammatory breast cancer, metastatic breast cancer, medullary carcinoma, tubular carcinoma, or mucinous carcinoma. Additionally, the breast cancer may be HER2-positive. In a particular embodiment, the patient possesses metastatic breast cancer.

Subjects treated in accordance with the present methods that possess breast cancer may also have received prior treatment with one or more chemotherapeutic agents. For example, the subject may possess metastatic breast cancer and have undergone prior chemotherapy with one or more of the following: a taxane drug such as docetaxel or paclitaxel; an anthracycline such as epiribuicin, doxorubicin, or mitoxantrone; capecitabine, bevacizumab, or trastuzumab.

All articles, books, patents, patent publications and other publications referenced herein are incorporated by reference in their entireties. In the event of an inconsistency between the teachings of this specification and the art incorporated by reference, the meaning of the teachings and definitions in this specification shall prevail (particularly with respect to terms used in the claims appended herein). For example, where the present application and a publication incorporated by reference define the same term differently, the definition of the term shall be preserved within the teachings of the document from which the definition is located.

EXAMPLES

It is to be understood that while the invention has been described in conjunction with certain preferred and specific embodiments, the foregoing description as well as the examples that follow are intended to illustrate and not limit the scope of the invention. Other aspects, advantages and modifications within the scope of the invention will be apparent to those skilled in the art to which the invention pertains.

Etirinotecan pegol ("4-arm-PEG-gly-irino-20K") is obtained from Nektar Therapeutics (San Francisco, Calif.). Preparation of the foregoing compound is described in U.S. Pat. No. 8,263,062.

SN-38 was obtained from a commercial source.

Example 1

Determination of Optimal In Vitro Concentrations of SN-38 and Gemcitabine by Cytotoxicity Assay The cell lines NCI-H460, HCT116, HT29, SkBr3 and HL60 cells were treated for 72 hours with either SN-38, the active metabolite of the topoisomerase-I inhibitor, irinotecan, or with the anticancer agent, gemcitabine. Gemcitabine inhibits thymidylate synthetase, leading to inhibition of DNA synthesis and cell death. The cells were treated at concentrations of 0.01, 0.1, 1 and 10 µM in triplicate with appropriate controls.

A MTT cytotoxicity assay was performed. Optical density (OD) was determined for each sample, and $IC_{50}$ values were determined (Graphpad Prism software using 4-parameter, non-linear curve fitting) for each drug relative to each cell line. The dose response of SN-38 and gemcitabine in the different cell lines was plotted. Good dose response was observed for SN-38 and gemcitabine in both the H460 and HL60 cell lines, and high and low concentrations of drug were determined for subsequent studies.

Example 2

Effect of Chemotherapeutic Agents, SN-38 and Gemcitabine, on DNA Damage Pathway Markers in Cell Lines Treated Ex-Vivo This study was carried out to monitor the modifications and identify potentially useful DNA damage biomarkers in cancer cell lines treated ex vivo with SN-38 and gemcitabine. SN-38 was selected as one of the chemotherapeutic agents of choice due to its being the active metabolite of the topoisomerase-I inhibitor, irinotecan, as well as of the long-acting, polymer-modified irinotecan molecule, etirinotecan pegol ("4-arm-PEG-gly-irino-20K"), as well as for its compatibility and effectiveness when examined in cell culture.

The cell lines, H460, HCT116, and HL60 were used in the study. H460 (30,000 cells/well) and HCT116 (15,000 cells/well) were grown in three 48 well plates. HL60 suspension cells were grown in five 25 cm flasks ($1 \times 10^6$ cells/flask). Cells were treated with the following two concentrations of gemcitabine and SN-38:

TABLE 1

Concentrations of Chemotherapeutic Agent Employed

| Cell line | Concentration, µM Gemcitabine | Concentration µM SN-38 |
|---|---|---|
| H460 | 0.01 | 1.0 |
| HCT116 | 0.5 | 10 |
| HL60 | 0.005 | 1.0 |

Cells treated with DMSO (final concentration 0.01%) were used as the control. Following 24 hours of drug treatment, cells were washed and fixed at 0 hour, 6 hour, and 24 hour timepoints. Cells were then stained for detection of the following markers: γ-H2AX, survivin, BRCA1, BRCA2, FAD51, and ATM. Expression levels for each biomarker were determined based upon mean fluorescence intensity (MFI) by laser scanning cytometry (iCys).

TABLE 2

Percent Change in Number of Positive Cells and Biomarker Expression Level Of NCI-H460 Cells Treated with 0.01 µM SN-38

| | 24 hr drug | | 24 hr drug + 6 hr without drug | | 24 hr drug + 24 hr without drug | |
|---|---|---|---|---|---|---|
| Biomarker | % change of positive cells | % change in MFI* | % change of positive cells | % change in MFI* | % change of positive cells | % change in MFI* |
| γH2AX | 235% | 1% | 919% | −7% | 328% | −77% |
| Survivin | −18% | 149% | 4% | 203% | 85% | 210% |
| BRCA1 | 143% | −8% | −52% | −10% | 3700% | 162% |
| BRCA2 | 131% | −20% | 8% | −16% | 261% | 263% |
| RAD51 | 180% | −8% | 337% | 120% | 60% | 32% |
| ATM | 13% | 120% | 88% | 329% | 105% | 41% |

TABLE 3

Percent Change in Number of Positive Cells and Biomarker Expression Level Of NCI-H460 Cells Treated with 0.01 µM Gemcitabine

| | 24 hr drug | | 24 hr drug + 6 hr without drug | | 24 hr drug + 24 hr without drug | |
|---|---|---|---|---|---|---|
| Biomarker | % change of positive cells | % change in MFI* | % change of positive cells | % change in MFI* | % change of positive cells | % change in MFI* |
| γH2AX | 204% | 3% | 1235% | 40% | 1834% | 288% |
| Survivin | −32% | −32% | 1% | 223% | −14% | 457% |
| BRCA1 | 162% | −3% | −54% | 18% | 3750% | 206% |
| BRCA2 | 130% | −43% | 6% | −28% | 167% | 296% |
| RAD51 | 62% | 7% | 613% | 127% | 260% | 23% |
| ATM | −28% | 125% | 80% | 438% | 40% | 151% |

For the H460 and HCT solid tumor cell lines, dose-dependent, drug induced increases in biomarker expression were observed (% and MFI).

For the HL60 leukemic cell line, biomarker expression was mostly unchanged or reduced after drug treatment as follows. Survivin showed a downward trend and a high percentage of TUNEL-positive cells was observed after 24 hour drug treatment. HL-60 cells were highly sensitive to both drugs based on the MTT data. It was postulated that drug concentration or treatment time may not have been optimal to detect increases in biomarker expression.

Markers observed to demonstrate an increase in positive percentages of cells were γ-H2AX, BCRA1, and RAD51. Markers observed to demonstrate an increase in MFI were BCRA2, ATM, and survivin. As a result of this study, markers determined to be suitable candidates for ex vivo treatment of cancer patient blood cells were were γ-H2AX, ATM (MFI) and RAD51.

Example 3

Analysis of Biomarkers in Circulating Tumor Cell (CTCs) after Ex Vivo Treatment with SN-38

The study was carried out to determine the effect of treatment with SN-38 on DNA damage pathway markers in isolated CTCs from solid tumor patient samples treated ex vivo.

Blood samples (10 mL) from three metastatic breast cancer patients was collected into EDTA preservative tubes (3 tubes per patient). Samples were treated as follows: Tube 1: Control DMSO only (final concentration 0.05%); Tube 2: SN-38 4 ng/ml (average clinical plasma $C_{max}$ concentration, repeat dose); Tube 3: SN-38 400 ng/ml (predicted tumor concentration). Sample tubes were incubated at 37° C. for 24 hours. Following treatment, blood was transferred to Cell-Save® preservative tubes and incubated for 30 minutes. CTCs were then isolated using the CellSearch® Profile kit, and fixed with 2% paraformaldehyde. Each sample was divided into 3 spots and cells were stained for the following markers: γH2AX, survivin, RAD51, ATM, TUNEL. The expression level of each biomarker was measured in terms of percent positive cells and mean fluorescence intensity (MFI) by laser scanning cytometer (iCys) (plots not shown).

Drug-induced, dose-dependent increases in ATM and RAD51 expression (MFI and % positive cells) were observed in 1 of 3 patients. Survivin and γH2AX expression were mostly reduced after drug treatment. Drug-induced, dose dependent increase in % TUNEL cells was observed in 2 of 3 patients.

Potential markers for monitoring drug effect to SN-38 treatment were identified and included ATM (MFI and % positive cells), RAD51 (MFI and % positive cells) and TUNEL (% dead cells).

Example 4

Circulating Tumor Cell (CTC)-Based Assay Development and Qualification Using Tumor Cell Lines and PBMCs from Healthy Volunteers The study was conducted to develop and qualify an antibody staining panel for laser scanning cytometry (LSC) multiplexing analysis of topoisomerase I, γH2AX, RAD51, Ki-67, topoisomerase II and ABCG2 and TUNEL on circulating tumor cells using tumor cell lines as a model.
Biomarker Qualification Primary and secondary antibodies were obtained from commercial sources. Control (0.1% DMSO) and drug-treated (SN-38, 10 uM) tumor cell lines and peripheral blood mononuclear cells (PBMCs) from healthy donors were used for biomarker qualification. The cell lines employed were as follows: HCT 116 (human colon carcinoma), MCF7 (human breast adenocarcinoma), A549 (human lung carcinoma), and SK-BR-3 (human breast adenocarcinoma, derived from metastatic site).

The biomarkers selected for the study included Topoisomerase I, γ-H2Ax, RAD51, Ki-67, Topisomerase ii, ABCG2, and TdT (also referred to as DNA nucleotidylexotransferase (DNTT).

Colorectal HCT-116 tumor cell lines treated with drug (SN-38, 10 µM) or DMSO (0.1%) were used as positive and negative controls, respectively, for the assay development for topoisomerase I and γ-H2Ax. HCT-116 cells have been reported to have a high level of expression of topoisomerase I (Pfister, T. H. et al., 2009, *Molecular Cancer Therapeutics*, 2009 8 (7), 1878-1884). MCF7 and A549 cells express moderate and low levels of topoisomerase I. HCT116 cells (70% confluent) were treated with 10 µM SN38 or with 0.1% DMSO, in culture medium (McCoy's 5A+5% FBS+ 1% penicillin/streptomycin) and $CO_2$ at 37° C. for 24 hours in a 75 $cm^2$ flask (BD Falcon). After incubation, cells were detached using 0.25% trypsin for 2-5 minutes, washed, counted, fixed with 2% PFA for 20 minutes, and cytospun onto glass slides.

A549 lung cancer cell lines and PBMCs from healthy donors were used as positive and negative biological controls for the assay development of topoisomerase II and ABCG2. A549 cells (70% confluent) were detached using 0.25% trypsin for 2-5 minutes, washed, counted, fixed with 2% PFA for 20 minutes, and cytospun onto glass slides.

Colorectal HCT-116 tumor cell lines treated with drug (SN-38, 10 µM) or DMSO (0.1%) were used as positive and negative controls for the assay development of RAD51. HCT116 cells (70% confluent) were treated with 10 µM SN38, or with 0.1% DMSO, in culture medium (McCoy's 5A+5% FBS+1% penicillin/streptomycin) and incubated at 37° C. for 24 hours in a 75 cm2 flask (BD Falcon). After incubation, cells were detached using 0.25% trypsin for 2-5 minutes, washed, counted, fixed with 2% PFA for 20 minutes, and cytospun onto glass slides.

Lung cancer cell line A549 and PBMCs from healthy donors were used as positive and negative biological controls in the assay development of Ki-67. A549 cells (70% confluent) were detached using 0.25% trypsin for 2-5 minutes, washed, counted, fixed with 2% PFA for 20 minutes, and cytospun onto glass slides.

For each marker, one to three different antibodies were tested. Staining was performed as follows. Briefly, cells were permeabilized with 0.2% triton X for 5 minutes, stained with 100 µL of primary antibody (biomarker specific or isotype control) at 4° C. overnight. After incubation, cells were washed twice with PBS. For indirect staining, secondary antibody reagent was added and incubated for 2 hours at room temperature. After washing, DAPI was added to visualize the nuclei. Cells were cover slipped and fluorescence intensity was quantified using iCys (CompuCyte, Westwood, Mass.). Cells were examined on an iCys equipped with 405, 488 and 633 lasers using standard operating procedure (SOP LM38). For analysis, iCys 3.4.12 software was used following the standard procedure for CTC analysis (SOP LM53). Briefly, nucleated cells were contoured by DAPI, and mean fluorescence intensity (MFI) was measured and reported for each biomarker.

Signals of biomarker staining were compared to secondary antibody staining only and isotype controls were processed in the same experiment. The antibody with the highest mean fluorescent intensity (MFI) was then selected for further development, with preference given to mono- over polyclonal antibodies. Titration was performed to identify the optimal dilution. Specificity was tested in positive and negative biological controls.

The optimal antibody for each biomarker was then multiplexed in a panel with antibodies against cytokeratin (CK), CD45 and DAPI (4',6-diamidino-2-phenylindole fluorescent dye) to form the panels to be used for phenotypic identification of circulating tumor cells. Multiplexed assay performance was tested using a mixture of tumor cells and peripheral blood mononuclear cells.

To investigate the robustness of the performance of the staining panels, the mean, standard variation, and % CV of staining of the markers were measured for all 26 slides. A summary of the assay development and qualification results is provided in Tables 4 to 7 below.

TABLE 4

Biomarker Assay Qualification—Staining Panel 1

| | Staining Panel 1 | |
|---|---|---|
| | Top 1 | γ-H2Ax |
| Antibody | | |
| Vendor | Abcam | Milipore |
| Catalogue # | Ab28432 | 16-193 |
| Clone | NA | JBW301 |
| Antibody | Rabbit polyclonal | Mouse Mab IgG1 |

TABLE 4-continued

Biomarker Assay Qualification—Staining Panel 1

| | Staining Panel 1 | |
|---|---|---|
| | Top 1 | γ-H2Ax |
| Conjugation | unconjugated | Biotin |
| Dilution | 1/200 | 1/200 |
| Biologic Controls | | |
| High, MFI (x10³) | HCT116, 964 | HCT116 (SN38), 487 |
| Low, MFI (x10³) | A549: 685 | HCT116 (DMSO), 124 |
| MFI Negative Control (x10³) | 7 | 113 |
| Reproducibility (n = 27) | | |
| % CV % Positive Cells | 1.4 | 15.5 |
| % CV MFI | 0.2 | 15.4 |
| Inter-day Variability (n = 3) | | |
| % CV % Positive Cells | 2.2 | 18 |
| % CV MFI | 4.4 | 23 |
| Inter-tech Variability (n = 3) | | |
| % CV % Positive Cells | 1.8 | 11 |
| % CV MFI | 9.4 | 15 |

TABLE 5

Biomarker Assay Qualification—Staining Panel 2

| | Staining Panel 2 | |
|---|---|---|
| | RAD51 | Ki-67 |
| Antibody | | |
| Vendor | Abcam | eBiosciences |
| Catalogue # | AB63801 | 51-5699 |
| Clone | NA | 20Raj1 |
| Antibody | Rabbit polyclonal | Mouse-monoclonal |
| Conjugation | unconjugated | Alexa Fluor 647 |
| Dilution | 1/200 | 1/50 |
| Biologic Controls | | |
| High, MFI (x10³) | HCT116 (SN38), 948 | A549, 1071 |
| Low, MFI (x10³) | HCT116 (DMSO), 178 | PBMC, 40 |
| MFI Negative Control (x10³) | 31 | na |
| Reproducibility (n = 27) | | |
| % CV % Positive Cells | 7.9 | 1.7 |
| % CV MFI | 22 | na |
| Inter-day Variability (n = 3) | | |
| % CV % Positive Cells | 11 | 1.7 |
| % CV MFI | 24 | na |
| Inter-tech Variability (n = 3) | | |
| % CV % Positive Cells | 12 | 1.8 |
| % CV MFI | 15 | na |

TABLE 6

Biomarker Assay Qualification—Staining Panel 3

| | Staining Panel 3 | |
|---|---|---|
| | Top 2 | ABCG2 |
| Antibody | | |
| Vendor | Epitomics | R&D Systems |
| Catalogue # | 1826-1 | BAM995 |
| Clone | EP1102Y | 5D3 |

TABLE 6-continued

Biomarker Assay Qualification—Staining Panel 3

| | Staining Panel 3 | |
| --- | --- | --- |
| | Top 2 | ABCG2 |
| Antibody Conjugation | Rabbit monoclonal unconjugated | Mouse Mab IgG1 Biotin |
| Dilution | 1/200 | 1/25 |
| Biologic Controls | | |
| High, MFI (x$10^3$) | SKBr3, 624 | A549, 365 |
| Low, MFI (x$10^3$) | MCF7, 436 | PBMCs, 91 |
| MFI Negative Control (x$10^3$) | 62 | 67 |
| Reproducibility (n = 27) | | |
| % CV % Positive Cells | 11 | 23 |
| % CV MFI | 17 | 19 |
| Inter-day Variability (n = 3) | | |
| % CV % Positive Cells | 13 | 20 |
| % CV MFI | 16 | 20 |
| Inter-tech Variability (n = 3) | | |
| % CV % Positive Cells | 6 | 20 |
| % CV MFI | 16 | 24 |

TABLE 7

Biomarker Assay Qualification—TUNEL

| | TUNEL TdT |
| --- | --- |
| Antibody | |
| Vendor | Promega |
| Catalogue # | rTdT |
| Clone | G3250 |
| Antibody | NA |
| Conjugation | dUTP-Cy5 (GE-PA55022) |
| Dilution | |
| Biologic Controls | |
| High, MFI (x$10^3$) | DNAse I Treated HCT116 |
| Low, MFI (x$10^3$) | Untreated HCT116 |
| MFI Negative Control (x$10^3$) | NA |
| Reproducibility (n = 27) | |
| % CV % Positive Cells | NA |
| % CV MFI | NA |
| Inter-day Variability (n = 3) | |
| % CV % Positive Cells | NA |
| % CV MFI | NA |
| Inter-tech Variability (n = 3) | |
| % CV % Positive Cells | NA |
| % CV MFI | NA |

The above staining panels were developed and qualified for use in the processing of clinical samples.

Example 5

Identification of Target-Specific Pharmacodynamic Biomarkers in Circulating Tumor Cells (CTCs) Obtained From Patients Metastatic Breast Cancer For clinical study-based data points, serial 7.5 mL whole blood samples were drawn from the patients and further processed. Results from baseline (pre-dose) samples are presented below.

PBMCs were separated and CTCs were isolated from the whole blood samples using ApoStream™ technology. ApoStream™ is a device (ApoCell, Inc. Houston, Tex.) which provides separation of circulating tumor cells from peripheral blood mononuclear cells based upon differences in morphology and dielectric properties. The process relies on a microchannel flow field to isolate CTCs using dielectrophoresis field flow fractionation (DEP-FFF), as described in detail in Gupta, et al., *Biomicrofluidics* 6, 024133 (2012), the contents of which is expressly incorporated herein by reference in its entirety. See, e.g., FIG. 1, which provides a schematic diagram of the ApoStream™ device, where the inset shows cell flow and separation in the flow chamber.

The CTCs obtained were stained for the pharmacodynamic markers described above and analyzed using an iCys laser scanning cytometer equipped with image analysis software. All assays were performed on an iCys laser scanning cytometer (CompuCyte, Westwood, Mass.) equipped with iCys 3.4.12 image analysis software.

TABLE 8

Statistics Based on 167 Pre-Dose Samples

| Successfully Processed 99% of Samples | Detectable CTCs 93% of Samples | Median # CTCs (Range) 217 (7.5-15000) | Top 1 | γ-H2Ax | RAD51 | Ki-67 | Top 2 | ABCG 2 | Tunel |
| --- | --- | --- | --- | --- | --- | --- | --- | --- | --- |
| % Cells Marker Positive | | | 82 | 16 | 53 | 52 | 89 | 31 | 93 |
| Range of Cells Marker Positive (%) | | | 1-100 | 1-25 | 1-100 | 1-100 | 1-100 | 1-100 | 1-100 |
| Range of Marker MFI (x$10^3$) | | | 85-2420 | 150-5144 | 109-1786 | NA | 127-7252 | 47-4187 | NA |

The above demonstrates that target-specific pharmacodynamic biomarkers have been identified and can be reliably measured in CTCs isolated from patients.

For the treatment phase of the clinical study, which is an open-label, randomized, parallel, two arm, multicenter, international phase III study, pentaerythritolyl-4-arm-(PEG-1-methylene-2 oxo-vinylamino acetate linked-irinotecan)-20K ("4-arm-PEG-gly-irino-20K") versus a "physician's choice" chemotherapeutic drug is administered to patients with locally recurrent or metastatic breast cancer (MBC). The patients have been previously treated with at least two and a maximum of five prior cytotoxic chemotherapy regimens with drugs including an anthracycline, a taxane, and capecitabine. The study randomizes approximately 840 patients using a 1:1 randomization ratio.

In Arm A, 4-arm-PEG-gly-irino-20K is administered at a dose level of 145 mg/m$^2$ on a q21d schedule. The chemotherapeutic is administered as a 90-minute IV infusion on Day 1 of each treatment cycle. In Arm B, the physician's drug of choice (limited to one of the following agents: eribulin, ixabepilone, vinorelbine, gemcitabine, or a taxane (paclitaxel, docetaxel or nab-paclitaxel) is administered per standard of care. Nab-paclitaxel is nanoparticle albumin-bound paclitaxel (brand name is Abraxane®, Celgene Corporation). Patients randomized to the physician's choice receive single-agent IV therapy (not combination therapy).

For biomarker data collected over the course of treatment, correlation of biomarker data with response, including RECIST response, event free survival, progression-free survival, and overall survival, is carried out using any of a number of statistically relevant methods. For example, boxplots may be used to compare the expression levels between responder and non-responder groups. Response parameters such as PFS and OS are stratified by quartiles of expression levels for comparison. Receiver Operating Characteristics (ROC) curve analysis is then employed to determine the optimal biomarker intensity threshold to allocate patients to high or low expressing groups predictive of response. Thresholds identified are tested for significance with regard to response rate using logistic regression. Other relevant measures of efficacy (event-free survival, progression-free survival, overall survival) are compared between patients with expression levels below or above the identified thresholds. Cox regression analysis is then performed to assess and quantify the significance of multiple predictors.

Example 6

Evaluation of Efficacy and Safety of Two Different Dosing Schedules of Pentaerythritolyl-4-Arm-(PEG-1-Methylene-2 Oxo-Vinylamino Acetate Linked-Irinotecan)-20K in Patients with Previously Treated Metastatic Breast Cancer Seventy patients were enrolled in the trial (n=35 per arm). The median patient age was 54.5 years (range, 33-83 years), ECOG performance status was zero in 40% and 1 in 60%, the median time since initial diagnosis to chemotherapeutic drug administration was 4.5 years (range, 0-19 years), and the median number of cytotoxic regimens for MBC was 2. All patients had previously received treatment with a taxane (76% docetaxel; 40% paclitaxel); 89% had received a prior anthracycline (63% epirubicin; 24% doxorubicin and one patient with mitoxantrone); and 27% of patient had received capecitabine. Fifteen (21.4%) patients had received prior bevacizumab. Among five patients with HER2-positive disease, all had received prior trastuzumab; none had received prior lapatinib.

Patients were randomized 1:1 into two treatment arms, comparing the same dose with a different dosing frequency. 4-arm-PEG-gly-irino-20K was administered at 145 mg/m$^2$ every 14 days (q14d) or every 21 days (q21 d) as an intravenous infusion over 90 minutes on day 1. Patients received treatment until disease progression or unacceptable toxicity. The drug dosage was dose-reduced by 25 mg/m$^2$ for grade 3-4 hematologic toxicity, grade 3-4 diarrhea, and other grade 2-4 non-hematologic toxicities (other than alopecia, anorexia, asthenia, and untreated nausea/vomiting). Protocol retreatment criteria required that toxicities and hematologic parameters were resolved to the following grades or levels prior to administration of the next dose: diarrhea, fully resolved; other non-hematologic toxicities, grade 1; neutrophils≥1,500/mm$^3$; platelets≥100,000/mm$^3$; and hemoglobin≥9 g/dL.

Medical history was taken at screening and on day 1 of each cycle. Physical exam was performed and serum CA27.29, complete blood count with differential, and serum chemistry were analyzed at screening, on day 1 of each cycle, and at end of treatment. Coagulation parameters were analyzed at screening and on day 1 of each cycle. Radiologic exam (either computed tomography or magnetic resonance imaging, with the same method per lesion used throughout the study) occurred at screening (within 28 days of day one, cycle 1) and approximately every 6 weeks thereafter until progressive disease, start of new anticancer therapy, or end of study. Patients were contacted approximately every 3 months after the end-of-treatment visit to assess progression (in the absence of progression on study), survival, receipt of subsequent anti-cancer therapy, and resolution of toxicity.

Response was measured by RECIST version 1.0 (Therasse, P., et al., 2000, *Journal of the National Cancer Institute*, 92 (3), 205-216) and toxicities were graded according to the National Cancer Institute Common Terminology Criteria for Adverse Events (NCI-CTCAE) version 3.0.

The primary endpoint was ORR, with confirmation of all responses by a second imaging procedure at least 28 days from the initial observation of response. Secondary endpoints were PFS, overall survival (OS), 6-month and 1-year survival, and safety. Exploratory endpoints included change from baseline in CA27.29, UGT1A1 and ABCC2 polymorphism for correlation with select toxicities.

Three populations for analysis were defined: 1) intent-to-treat (ITT), 2) efficacy evaluable, and 3) safety. The ITT population was the primary population for all efficacy analyses and included all randomized patients. The efficacy evaluable population included all randomized patients with measurable disease that had at least one tumor assessment post study drug administration or had disease progression or died within 6 weeks of the first study drug administration. The safety population consisted of all patients who received at least one dose or partial dose of chemotherapeutic agent.

Summary statistics were used for continuous variables, frequency counts and percentages were used for categorical variables. Ninety-five percent confidence interval were calculated for ORR using the Exact method. Time-to-event variables were analyzed using the Kaplan-Meier method.

The chemotherapeutic agent, 4-arm-PEG-gly-irino-20K, substantially exceeded the efficacy threshold of this study, producing an objective response rate (ORR) of 28.6% when administered every 14 days or every 21 days. See Table 9 below.

TABLE 9

Efficacy Results in Patients with Metastatic Breast Cancer

| | Total |
|---|---|
| Overall Response Rate (ORR) | 29% (N = 66) |
| Progression Free Survival (PFS) | 4.6 months |
| | (5.3 months in q21d) |
| Overall Survival (OS) | 10.3 months |
| | (13.1 months in q21d) |
| Overall best CA27.29 response (50% or better decline in at least one observation from baseline) | 36% (16/45) |

It is claimed:

1. A method for predicting the efficacy of treatment with a DNA-damaging chemotherapeutic agent in a patient diagnosed with breast cancer and treating breast cancer, the method comprising:

isolating circulating breast tumor cells by dielectrophoresis field-flow fractionation from a blood sample obtained from the patient, determining a baseline expression level of one or more proteins selected from the group consisting of topoisomerase I, RAD51, Ki-67, and ABCG2 in the isolated circulating breast tumor cells prior to treatment of the patient with a chemotherapeutic agent to thereby predict the responsiveness of the tumor cells to treatment with the DNA-damaging chemotherapeutic agent, wherein for topoisomerase I, elevated baseline expression levels indicate a predisposition to responsiveness to treatment with the DNA-damaging therapeutic agent and suppressed baseline expression levels indicate a predisposition for unresponsiveness to treatment with the DNA-damaging therapeutic agent;

for RAD51, elevated baseline expression levels indicate a predisposition for unresponsiveness to treatment with the DNA-damaging agent and suppressed baseline expression levels indicate a predisposition to responsiveness to treatment;

for Ki-67, elevated baseline expression levels indicate a predisposition to responsiveness to treatment with the DNA-damaging therapeutic agent and suppressed baseline expression levels indicate a predisposition for unresponsiveness to treatment, for ABCG2, elevated baseline expression levels indicate a predisposition for unresponsiveness to treatment with the DNA-damaging agent and suppressed baseline expression levels indicate a predisposition to responsiveness to treatment, wherein determining whether a baseline expression level of the protein is elevated or suppressed is based upon a comparison to the mean and/or median baseline expression level of the protein in circulating tumor cells of the overall study population, and administering a therapeutically effective amount of the DNA-damaging therapeutic agent to the patient, wherein the DNA-damaging therapeutic agent comprises irinotecan modified by releasable covalent attachment to one or more poly(ethylene glycol) polymers.

2. The method of claim 1, wherein the DNA-damaging therapeutic agent is etirinotecan pegol.

3. The method of claim 1, wherein the cancer is metastatic breast cancer.

4. The method of claim 1, wherein the baseline expression levels of the one or more proteins and the expression levels of the one or more proteins following treatment are determined based upon the percentage of positive cells and/or mean fluorescent intensity of the circulating tumor cells stained for detection of the one or more proteins.

* * * * *